United States Patent [19]

Iwamatsu et al.

[11] 4,302,580
[45] Nov. 24, 1981

[54] PROCESS FOR THE PRODUCTION OF A CEPHAMYCIN DERIVATIVE

[75] Inventors: Katsuyoshi Iwamatsu; Jiro Itoh, both of Yokohama; Shoji Omoto, Tokyo; Takashi Tsuruoka, Kawasaki; Shigeharu Inouye, Yokohama, all of Japan

[73] Assignee: Meiji Seika Kaisha, Ltd., Tokyo, Japan

[21] Appl. No.: 185,594

[22] Filed: Sep. 9, 1980

[30] Foreign Application Priority Data

Sep. 17, 1979 [JP] Japan .................. 54/117911

[51] Int. Cl.$^3$ ........................... C07D 501/36
[52] U.S. Cl. ..................... 544/21; 424/246
[58] Field of Search .................. 544/21; 424/246

[56] References Cited

U.S. PATENT DOCUMENTS 4,077,965  3/1972  Kamiya et al. .............. 544/26

*Primary Examiner*—Nicholas S. Rizzo
*Attorney, Agent, or Firm*—Larson and Taylor

[57] ABSTRACT

A chemotherapeutic, antibacterial agent, 7$\beta$-[(2D-2-amino-2-carboxy)ethylthioacetamido]-7$\alpha$-methoxy-3-[(1-methyl-1H-tetrazole-5-yl)thiomethyl]-3-cephem-4-carboxylic acid is produced economically and efficiently starting from cephamycin A and/or B by a "new route" process comprising the consecutive steps of reaction of cephamycin with 5-mercapto-1-methyl-1H-tetrazole; protection of the terminal amino group thereof by acylation; protection of the two carboxyl groups thereof by esterification; replacement of the acyl group initially having attached to the 7-amino group by a halogenoacetyl group; deprotection of the blocked 4-carboxyl group; and condensation of D-cysteine with the halogenoacetyl group attaching to the 7-amino group.

9 Claims, No Drawings

PROCESS FOR THE PRODUCTION OF A CEPHAMYCIN DERIVATIVE

BACKGROUND OF THE INVENTION

This invention relates to a new process for the production of a compound of cephamycin type and specifically of 7β-[(2D-2-amino-2-carboxy)ethylthioacetamido]-7α-methoxy-3-[(1-methyl-1H-tetrazole-5-yl)thiomethyl]-3-cephem-4-carboxylic acid and a pharmaceutically acceptable salt thereof as well as a pharmaceutically acceptable ester thereof which possess a high antibacterial activity and find wide applications in chemotherapeutic treatment of bacterial infections.

The 7β-[(2D-2-amino-2-carboxy)ethylthioacetamido]-7α-methoxy-3-[(1-methyl-1H-tetrazole-5-yl)thiomethyl]-3-cephem-4-carboxylic acid (hereinafter referred to merely as "the object compound") was newly synthetized in the laboratory where the present inventors are working (see Japanese patent application unexamined publication "Kokai" No. 83791/80 published on 24th June 1980; Belgian Pat. No. 880,656; co-pending U.K. patent application No. 79 43159; and co-pending U.S. patent application Ser. No. 104,220). All of the methods of producing the object compound which were developed earlier are exclusively starting from 7-amino-cephalosporanic acid as the initial material and need in a certain stage to carry out some known procedures for the 7α-methoxylation of the 7-amino-cephalosporanic acid. The presently available procedures for the 7α-methoxylation usually need careful and troublesome operations and are accompanied inevitably by undesirable 7β-methoxylation. The concomitance of the desired 7α-methoxylation product with even a slight amount of the undesired 7β-methoxylation product normally can reduce very much the therapeutic effect and commerical value of the 7α-methoxylation product, and hence it is strongly demanded to remove the 7β-methoxylation product from the 7α-methoxylation product. However, there is not yet obtained an efficient and facile method of purifying the 7α-methoxylation product to be freed from the concomitant 7α-methoxylation product which is available in a commercial scale. In these circumstances, we have sought for a new process for the production of the object compound which is unnecessary in any stage to conduct the procedures for the 7α-methoxylation of 7-amino-cephalosporanic acid or a 7-amino-cephalosporine compound. Cephamycin A or B is the compound initially containing the 7α-methoxycephem nucleus which is produced as the fermentative product in the cultivation of some microorganisms belonging to the genus Streptomyces, and we have extensively studied in an attempt to provide a new process of producing the object compound which is able to start from cephamycin A or B and hence does not need the 7α-methoxylation taking place in any stage of the process. As a result, we have now found that when cephamycin A and/or cephamycin B are or is subjected to consecutive steps of reactions which are combined in an ingenious way as described hereinafter, the object compound can be produced in a facile way in a high yield. On the basis of these our findings, we have now devised the new process of this invention.

A principal object of this invention is to provide a new process whereby the desired object compound can be advantageously produced starting from cephamycin A, B but without necessity of the 7α-methoxylation step which has been required in the earlier methods starting from 7-amino-cephalosporanic acid.

Other objects and advantages of this invention will become apparent from the following descriptions.

SUMMARY OF THE INVENTION

According to this invention, there is provided a process for the production of 7β-[(2D-2-amino-2-carboxy)ethylthioacetamido]-7α-methoxy-3-[(1-methyl-1H-tetrazole-5-yl)thiomethyl]-3-cephem-4-carboxylic acid which comprises the consecutive steps of:

(a) reacting cephamycin A and/or cephamycin B with 5-mercapto-1-methyl-1H-tetrazole to produce the compound of the formula (I)

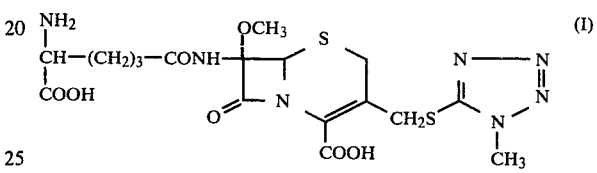

(b) reacting the compound (I) with an acylating agent for introduction of an amino-protecting group to produce a compound of the formula (II)

$$\begin{array}{c}\text{NHR}\\|\\\text{CH}-(\text{CH}_2)_3-\text{CONH}\\|\\\text{COOH}\end{array}\quad\begin{array}{c}\text{OCH}_3\quad\text{S}\\\diagup\quad\diagdown\\\diagdown\quad\text{N}\\\text{O}\diagdown\quad\diagup\quad\text{CH}_2\text{S}\\\text{COOH}\end{array}\begin{array}{c}\text{N}\longrightarrow\text{N}\\\parallel\\\text{N}\diagdown\quad\text{N}\\|\\\text{CH}_3\end{array}\quad(\text{II})$$

wherein R represents the amino-protecting group of acyl type, (c) reacting the compound (II) with a reagent for introduction of a carboxyl-protecting group to block the two carboxyl groups of the compound (II) and produce the compound of the formula (II')

$$\begin{array}{c}\text{NHR}\\|\\\text{CH}-(\text{CH}_2)_3-\text{CONH}\\|\\\text{COOH}\end{array}\quad\begin{array}{c}\text{OCH}_3\quad\text{S}\\\diagup\quad\diagdown\\\diagdown\quad\text{N}\\\text{O}\diagdown\quad\diagup\quad\text{CH}_2\text{S}\\\text{COOR'}\end{array}\begin{array}{c}\text{N}\longrightarrow\text{N}\\\parallel\\\text{N}\diagdown\quad\text{N}\\|\\\text{CH}_3\end{array}\quad(\text{II'})$$

wherein R' represents the carboxyl-protecting group, (d) reacting the compound (II') with a halogenoacetyl halide of the formula $$\text{XCH}_2\text{COX}'$$

wherein X and X', which may be the same or different, each represents a halogen, particularly chlorine or bromine, in the presence of a molecular sieves material or in the presence of a silylating agent to produce a compound of the formula duced by microorganisms of several species of actinomycetes:

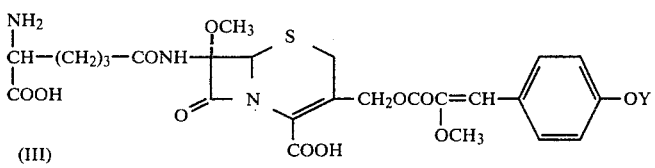

(III)

wherein Y is hydrogen for cephamycin A and is sulfonic acid group (—SO₃H) for cephamycin B.

We have developed and claimed a method for the purification of cephamycin A, B which is produced by cultivation of *Streptomyces viridochromogenes* SF-1584 strain (FERM-P No. 2284) (see Japanese patent application unexamined publication "Kokai" No. 64489/75) and a method for the N-acylation of the 7-acylamido group of the cephamycin A, B in the fermentation broth or filtrate (see Japanese patent application unexamined publication "Kokai" No. 64290/75).

In the latter method, the acylating agent as employed can be directly added to the fermentation broth or its filtrate containing cephamycin A, B produced and accumulated by cultivation of the SF-1584 strain or to a primary concentrate which is obtained by chromatographic concentration of the fermentation broth.

Cephamycin A, B is fairly unstable and readily hydrolisable in its aqueous solution, especially due to high susceptibility to hydrolysis of the 3-substitutent of cephamycin A, B. In account of this, the first step of the process according to this invention is so arranged that cephamycin A, B is at first converted into a more stable derivative thereof by reacting with 5-mercapto-1-methyl-1H-tetrazole to replace the readily hydrolisable 3-substitutent by the more stable 3-methyltetrazolylthiomethyl substituent. This is a unique feature of this invention. It is preferred in the first step of the present process that 5-mercapto-1-methyl-1H-tetrazole is reacted with cephamycin A, B in the earliest stage of the present process. To this end, 5-mercapto-1-methyl-1H-tetrazole is preferably admixed with the filtrate of the fermentation broth containing cephamycin A, B or at most with the primary concentrate of said fermentation broth filtrate, so that 5-mercapto-1-methyl-1H-tetrazole can be reacted with cephamycin A, B just while cephamycin A, B still remains in the fermentation broth filtrate or in said primary concentrate, before cephamycin A, B receives any substantial isolation or purification method. The aforesaid primary concentrate which may be used in the present process can be obtained either by passing the fermentation broth filtrate through a column of an adsorbent resin such as Amberlite XAD-2 (a product of Rohm & Haas Co., U.S.A.) or Diaion HP-20 (a product of Mitsubishi Kasei Co., Japan), followed by washing with water and elution with aqueous acetone or aqueous methanol or by extracting the fermentation broth filtrate at an acidic pH value of 1.5~3.0 with n-butanol.

In the first step of the present process, cephamycin A, B in the fermentation broth, its filtrate or the primary concentrate may be reacted with 5-mercapto-1-methyl-1H-tetrazole at an acidic or neutral pH value. The substitution reaction which takes place at the 3-position of cephamycin A, B in this first step may proceed at ambient temperature. However, the reaction may be effected at a temperature of 15°~60° C., and may preferably be

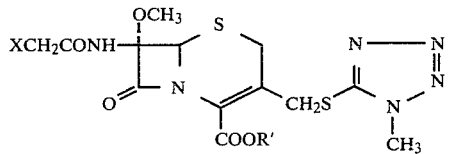

wherein X is as defined above and R' represents the carboxyl-protecting group as above, (e) removing the carboxyl-protecting group (R') from the compound (III) in a known manner to produce the compound of the formula (III')

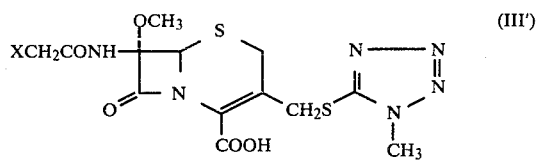

wherein X is as defined above, and (f) reacting the compound (III') with D-cysteine to produce the desired product. The expression "cephamycin A, B" is used herein to mean cephamycin A and/or cephamycin B, namely cephamycin A or B, or a mixture of the two.

In brief, according to the process of this invention, the object compound can be produced from cephamycin A, B by the following six stages of:

(a) reaction of cephamycin A, B with 5-mercapto-1-methyl-1H-tetrazole to introduce the methyltetrazolylthiomethyl group into the 3-position of the cephamycin A, B, (b) reaction of the cephamycin A, B derivative obtained in the stage (a) with an acylating agent to protect the terminal amino group present in the 7-acylacetamido side chain of the cephamycin A, B, (c) protection by esterification of the two carboxyl groups, namely the 4-carboxyl group and the terminal carboxyl group present in said 7-acylacetamido side chain, (d) halogenoacetylation at the 7-amino group, with concurrent removal of the acyl group initially having attached to the 7-amino group of the cephamycin A, B, (e) removal of the protecting group from the blocked 4-carboxyl group, and (f) introduction of the D-cysteine moiety into the halogenoacetyl group attaching to the 7-amino group.

If the carboxy-protecting (ester-forming) group at the 4-carboxyl group is cleavable by hydrolysis in vivo, the stage (e) for removal of the carboxyl-protecting group may be omitted, if desired. In this case, the final product is obtained in the form of the 4-carboxylate (ester).

DETAILED DESCRIPTION OF THE INVENTION

It is known that the starting material, cephamycin A, B having the following structural formula can be proaccelerated by heating to a temperature of 40° to 60° C., so that the reaction can be completed in 3~10 hours.

After the reaction is completed in the first step of the present process, the reaction solution may be concentrated to a smaller volume, if necessary.

In the second step of the present process, the reaction solution from the first step or a concentrated solution thereof containing the compound of the formula (I), namely the 7-(5-amino-5-carboxyvalerylamido)-3-[(1-methyl-1H-tetrazole-5-yl)thiomethyl]-3-cephem-4-carboxylic acid formed is reacted with an excess of an acylating agent which is known as a reagent for introduction of an amino-protecting group, in order to protect the terminal 5-amino group present in the 7-acylamino substituent of the cephamycin derivative of the formula (I). The acylating agent for this purpose may be, for example, in the form of an acid anhydride, acid halide or a halogenated derivative of a carbonic acid alkyl ester, an alkoxycarbonyl or aralkyloxycarbonyl halide and may preferably be methoxycarbonyl chloride, t-butoxycarbonyl chloride, trichloroethoxycarbonyl chloride or benzyloxycarbonyl chloride. The reaction in the second step of the present process may be conducted in an aqueous reaction medium when the reagents are soluble therein. When the acylating agent is somewhat sparingly soluble in water, as the case be with benzyloxycarbonyl halide, it is convenient that the reaction in the second step of the present process is carried out in the additional presence of a water-miscible organic solvent such as acetone, methanol and the like. The acylation for the protection of the terminal amino group may generally be carried out at ambient temperature or under cooling and preferably in the presence of an acid-binder such as a tertiary alkylamine e.g. triethylamine and alkali metal carbonate. The reaction time required in the second step of the present process is usually of the order of 1 hour to a few hours.

After the completion of the N-acylation in the second step, the resultant reaction solution may be concentrated by evaporation of the organic solvent present or may be diluted with water, then extracted under acidic conditions with a suitable organic solvent (e.g. ethyl acetate) and washed with water, followed by back-extraction into an aqueous weakly alkaline solution such as 5% aqueous sodium hydrogen carbonate. By this purification technique, the S-acylated derivative of 5-mercapto-1-methyl-1H-tetrazole which may be produced from the excess of the 5-mercapto-1-methyl-1H-tetrazole, and the unreacted excess of the acylating agent can easily be removed from the reaction mixture. Further treatment may be effected by passing the back-extraction extracts through an adsorptive resin such as Diaion HP-20 (a microporous, non-ionic adsorbent resin made of a styrene-vinylbenzene copolymer, a product of Mitsubishi Kasei Co., Japan) or Amberlite XAD-2 ( a microporous, non-ionic adsorbent resin made of a styrene-vinylbenzene copolymer, a product of Rohm & Haas Co., U.S.A.) whereby the unreacted 5-mercapto-1-methyl-1H-tetrazole and the acidic degraded products of the excessive acylating agent can readily be separated off. The desired N-protected product of the formula (II) obtained in the second step can be eluted from the adsorptive resin using aqueous acetone or aqueous methanol as eluent.

There is thus obtained the N-protected compound of above formula (II) which is stable and easy to purify, so that it can be purified, if necessary, by chromatographic technqiue using a basic ion-exchanger or silica gel.

As a matter of course, the use of cephamycin A, B in the first step leads to the production of the same compound (II), irrespectively of whether cephamycin A or B or a mixture thereof is used as the starting material. Thus, the significant feature of the first and second steps is in that a mixture of relatively unstable cephamycins A and B is converted, at an early stage of the present process, into the single compound (II) which is fairly stable and easy to purify.

In the third step of the present process, the two free carboxyl groups of the compound (II) are blocked with a carboxyl-protecting group to prevent undesirable side-reactions from taking place in the subsequent fourth step. The protecting group to be used may preferably be an ester-forming group and generally be any one which is well known in the field of synthetic cephalosporins, provided it is eventually removable under mild conditions without having any effect on the other sites in the cephem nucleus. Thus, for example, the introduction of the carboxyl-protecting group into the compound (II) may be achieved by the reaction of the latter with a reagent for introduction of the carboxyl-protecting group, for example, by the reaction with diphenyldiazomethane in an inert organic solvent to form the diphenylmethyl ester, by the reaction with isobutene in the presence of an acid catalyst to form the t-butyl ester or by the reaction with trichloroethyl chloride, methoxyethoxymethyl chloride or substituted benzyl bromide such as p-nitrobenzyl bromide in the presence of a base such as acid-binding agent to form the trichloroethyl ester, methoxyethoxymethyl ester or substituted benzyl ester, respectively.

The esterification as described just above for the purpose of protecting the carboxyl groups will be carried out for a period of time ranging from tens of minutes to several hours. It is noted that an excess of the base which is present in the esterification procedure as the acid-binding agent must not be used in order to avoid the translocation of the existing double bonds of the cephem compound.

The desired protected product (II') from the third step, which has became readily soluble in organic solvents, can be isolated from the reaction mixture by extraction with an appropriate organic solvent, followed by evaporation of the extract to dryness. The protected product can be purified, if necessary, by chromatography or countercurrent distribution method.

In the fourth step of the present process, the product of the formula (II') obtained in the third step which is the 7β-N-monoacyl form is reacted with the halogenoacetyl halide of the formula:

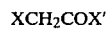

wherein X and X' independently represent halogen atom, especially chlorine or bromine atom, in the presence of a molecular sieves material or in the presence of a silylating agent. In this fourth step, the 7β-N-monoacyl compound (II') seems to be converted once into a 7β-N-diacyl compound from which is concurrently liberated the acyl group initially having attached to the 7-amino group of the starting cephamycin. Anyhow, in this fourth step, there takes place an acyl-exchange reaction that the acyl group initially having attached to the 7-amino group of the cephamycin is replaced by the halogenoacetyl group of the halogenoacetyl halide reagent employed, giving the compound of the formula (III). The presence of the molecular sieves material in this step serves to remove the hydrogen halide liberated in the above acyl-exchange reaction. The presence of the silylating agent serves to activate the amido group at the 7-position of the compound (II').

Examples of the molecular sieves material suitable for this purpose includes a synthetic zeolite having an average pore diameter of 3 Å, 4 Å or 5 Å which is commercially available under the trade name of "Molecular Sieves" 3Å, 4Å and 5Å from Linde Co. (U.S.A.). When the molecular sieves is present, the reaction may generally be carried out at a temperature of 15°~60° C. or preferably at a temperature of 40°~60° C., in an aprotic solvent such as halogenated alkanes or cyclic ethers.

The silylating agent may be any known one being conventionally used for silylation of active hydrogen and preferably includes N-silylamides, for example, N-(trimethylsilyl)acetamide, N,N-bis(trimethylsilyl) acetamide and N,N-bis(trimethylsilyl) trifluoroacetamide. Where the reaction is carried out in the presence of the silylating agent, it is preferably conducted at an elevated temperature of 40° to 60° C., though it may proceed at ambient temperature.

Examples of the halogenoacetyl halide suitable as the acetylating reagent include bromoacetyl bromide, bromoacetyl chloride, chloroacetyl bromide and chloroacetyl chloride.

The duration required for the reaction in the fourth step of the present process is usually between several hours and 20 hours.

The intermediate 7β-N-diacyl derivative produced during the course of the reaction in the fourth step will spontaneously decompose sequentially to give the 7β-N-monoacyl form of the formula (III) which has undergone the acyl-exchange reaction at the 7-amino group. In order to achieve a complete decomposition of the 7β-N-diacyl derivative into the 7β-N-monoacyl form, however, it is preferred to carry out an additional operation for removing the amino-protecting group (R) remaining at the terminal amino group of the 7β-N-diacyl derivative. This additional operation may be a reductive treatment with acetic acid and zinc powder for the removal of trichloroethoxycarbonyl or benzyloxycarbonyl group as the group R, or may be a hydrolytic treatment with an acid for the removal of t-butoxycarbonyl group as the group R.

In this way, the compound of above formula (III) is produced in the fourth step of the present process. The desired compound (III) can be separated from the reaction mixture by filtering off insoluble matters, washing the filtrate with water and distillating off the solvent and be purified, if necessary, by column chromatography.

The fifth step of the present process, is to regenerate the blocked 4-carboxyl group of the compound (III) into the free 4-carboxyl group. The deprotection operation to be employed will depend upon the nature of the carboxyl-protecting group which has been introduced in the third step. Thus, the deprotection can be accomplished, as the case may be, either by heating the methoxyethoxymethyl ester (carboxylate) together with methanol, or by contacting the t-butylester with a dilute mineral acid in a suitable inert solvent, or by reducing the substituted-benzyl ester in a suitable inert solvent in the presence of a palladium catalyst, or by interacting the diphenylmethyl ester with trifluoroacetic acid-/anisole or formic acid in an appropriate inert organic solvent, or by treating the trichloroethyl ester with zinc/acetic acid.

The compound (III) bearing such as carboxyl-protecting group (R'), as pivaloyloxymethyl group which is fairly stable from the viewpoint of chemistry but is readily cleavable by hydrolysis in vivo can be directly used in the subsequent step of introducing the D-cysteine moiety, without necessity of carrying out the above fifth step to remove the carboxyl-protecting group.

After the completion of the deprotection reaction in the fifth step, the desired deprotected product (III') can be recovered from the reaction mixture by a conventional procedure, for example, by filtering off insoluble matters if any, removing the solvent and the excess of the reagent(s) from the filtrate by distillation under reduced pressure, dissolving the residue in a suitable solvent, washing the solution with water and distillating off the solvent.

The final, sixth step of the present process consists in reacting the halogenoacetyl derivative of above formula (III') with D-cysteine of the formula HOOC—CH(NH$_2$)—CH$_2$SH to give the final desired product of the formula (IV) shown later where R" is a hydrogen atom. This condensation reaction may smoothly proceed under neutral conditions in an inert solvent, preferably water or an aqueous organic solvent. The reaction is generally carried out at ambient or reduced temperature for 1~5 hours.

For isolation and purification of the final compound (IV), the resultant reaction solution can be concentrated to a small volume and subjected to a treatment with gel-filtration agent for example, Sephadex G-10, LH-20 (a product of Pharmacia Chemical Co., Sweden), or to a chromatography on an adsorbent resin such as Amberlite XAD-2 (a product of Rohm & Haas Co., U.S.A.) and Diaion HP-20 (a product of Mitsubishi Kasei Co., Japan).

Where desired or required, the compound thus obtained in the sixth step of the present process can further be converted in a conventional manner into either its pharmaceutically acceptable salt with a pharmaceutically acceptable cation, for example, an alkali metal, alkaline earth metal, basic amino acid or amine or even into its in vivo active ester, for example, acyloxyalkyl, alkoxycarbonyloxyalkyl or alkoxy ester.

According to the process of this invention, therefore, there may generally be produced a compound of the formula:

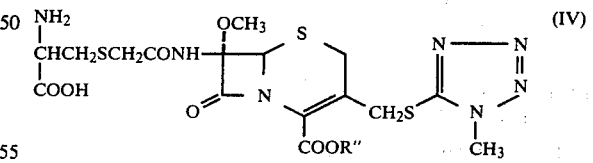

wherein R" represents a hydrogen atom, a pharmaceutically acceptable cation or a pharmaceutically acceptable ester-forming group which is readily cleavable by hydrolysis in vivo.

As state hereinbefore, when the 4-carboxyl group of the compound of the formula (III) given in the fourth step of the present process has been protected with such a carboxyl-protecting group which is a pharmaceutically acceptable ester-forming group cleavable readily in vivo, it is unnecessary to carry out the fifth step of removing the carboxyl-protecting group therefrom, and then the compound (III) of such kind may directly be subjected to the final step of reacting with the D-cysteine for the introduction of the D-cysteine moiety into the 7β-halogenoacetylamido group of the compound (III). According to a further aspect of this invention, therefore, there is provided a process for the production of a pharmaceutically acceptable ester of 7β-[(2D-2-amino-2-carboxy)ethylthioacetamido]-7α-methoxy-3-[(1-methyl-1H-tetrazole-5-yl)thiomethyl]-3-cephem-4-carboxylic acid which comprises the consecutive steps of:

(a) reacting cephamycin A and/or cephamycin B with 5-mercapto-1-methyl-1H-tetrazole to produce the compound of the formula (I)

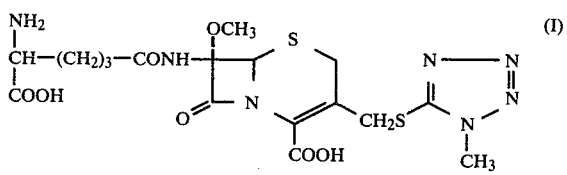

(b) reacting the compound (I) with an acylating agent for introduction of an amino-protecting group to produce a compound of the formula (II)

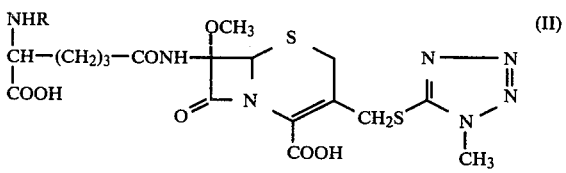

wherein R represents the amino-protecting group of acyl type, (c′) reacting the compound (II) with a reagent for introduction of an ester-forming group which serves as the carboxyl-protecting group and is pharmaceutically acceptable and cleavable by hydrolysis in vivo, to esterify the two carboxyl groups of the compound (II) and produce the compound of the formula (II″)

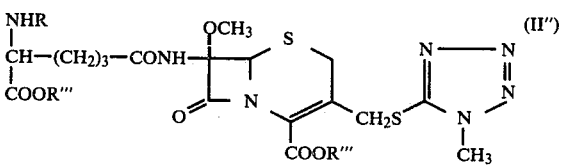

wherein R‴ is the pharmaceutically acceptable ester-forming group cleavable by hydrolysis in vivo and preferably be selected from an acyloxyalkyl group, an alkoxycarbonyloxyalkyl group and an alkoxyl group, especially pivaloyloxymethyl group, (d′) reacting the compound (II″) with a halogenoacetyl halide of the formula

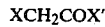

XCH₂COX′ wherein X and X′, which may be the same or different, each represents a halogen, particularly chlorine or bromine, in the presence of a molecular sieves material or in the presence of a silylating agent to produce a compound of the formula

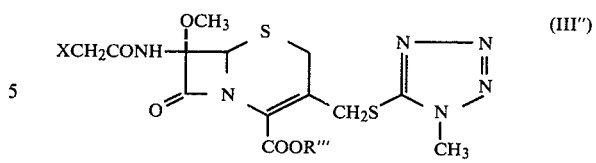

wherein X is as defined above and R‴ represents the ester-forming group as above, and (f′) reacting the compound (III″) with D-cysteine to produce the desired ester of the formula (IV′)

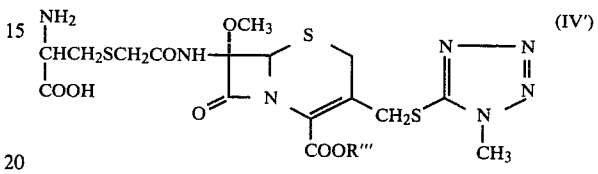

wherein R‴ is the ester-forming group as defined above.

This invention is further illustrated but not limited by the following Example.

EXAMPLE 1

(i) *Streptomyces viridochromogenes* SF-1584 strain (deposited under FERM-P 2288) was cultivated under aeration and agitation at 28° C. for 120 hours in a culture medium placed in a 50 l jar-fermentor. The culture medium comprised 1.5% glycerol, 1.5% dextrin, 2.0% soybean meal, 0.15% calcium carbonate and 0.05% sodium thiosulfate. The culture broth obtained was adjusted to pH 3 by addition of 5 N—HCl and filtered to give 20 l of a broth filtrate.

The broth filtrate containing cephamycin A, B was adjusted to a neutral pH value by addition of 3 N—NaOH and passed through a column of 2 of a microporous, non-ionic adsorbent resin, Amberlite XAD-2 (a product of Rohm & Haas Co., U.S.A.). The column was washed with 6 l of water and then eluted with 8 l of 50% aqueous acetone, immediately followed by addition to the eluate of a solution (pH 5.5) of 5-mercapto-1-methyl-1H-tetrazole (15 g) in water (50 ml). The mixture was agitated overnight at 35° C. and the resultant reaction solution was concentrated by evaporation to a volume of 500 ml. To the concentrated solution (containing 7β-(5-amino-5-carboxyvalerylamido)-7α-methoxy-3-[(1-methyl-1H-tetrazole-5-yl)thiomethyl]-3-cephem-4-carboxylic acid as formed) was added dropwise with stirring a solution of trichloroethoxycarbonyl chloride (18 ml) (an amino-protecting reagent) in acetone (200 ml), during which the resulting mixture was kept at pH 7.5~8.0 by addition of aqueous sodium carbonate. After completion of the addition, the mixture was agitated for 3 hours to perform the amino-protecting reaction.

Subsequently, the reaction solution was adjusted to pH 6 by addition of 5 N-HCl, concentrated by evaporation of the acetone, again adjusted to pH 2 by addition of 5 N—HCl under cooling and then extracted with 2×200 ml of ethyl acetate. The extracts combined were washed with HCl-acidified water (pH 2) and then subjected to back-extraction with 200 ml of 5% aqueous sodium bicarbonate solution. This operation was repeated once more. The final extract was adjusted to pH 6.0 by addition of 5 N—HCl and concentrated to a small volume. The concentrate was passed through a column of 500 ml of a microporous, non-ionic adsorbent resin, Diaion HP-20 (a product of Mitsubishi Kasei Co., Japan) and the column was washed with water and then eluted with 10% aqueous acetone. The eluate was concentrated and passed through a column of Amberlite XAD-2 (250 ml). The column was subjected to linear gradient elution with aqueous methanol. The active fractions of the eluate were combined together and concentrated to dryness to yield 800 mg of sodium 7β-(5D-5-trichloroethoxycarbonylamino-5-carboxyvalerylamido)-7α-methoxy-3-[(1-methyl-1H-tetrazole-5-yl) thiomethyl]-3-cephem-4-carboxylate.

This product was dissolved in 50 ml of water, to which was then added 50 ml of ethyl acetate and then an amount of 5 N hydrochloric acid under ice-cooling to adjust to pH 2.0. The ethyl acetate phase was separated off and the aqueous phase was extracted with ethyl acetate. The extract was combined with the ethyl acetate phase and the organic solution obtained was washed with aqueous saturated sodium chloride, dried over anhydrous sodium sulfate and concentrated to dryness to afford 700 mg of 7β-(5D-5-trichloroethoxycarbonylamino-5-carboxyvalerylamido)-7α-methoxy-3-[(1-methyl-1H-tetrazole-5-yl)thiomethyl]-3-cephem-4-carboxylic acid.

This product gave Rf value=0.58 when developed in a thin layer chromatography on silica gel using a solvent of n-butanol/acetic acid/water (2:1:1 by volume).

(ii) 5.2 g of the carboxylic acid product obtained in the above procedure (i) was dissolved in 100 ml of ethyl acetate, to which was then added dropwise under ice-cooling and stirring a solution of diphenyldiazomethane (3.9 g) (a carboxyl-protecting reagent) in 40 ml of ethyl acetate. After completion of the addition, the mixture was stirred for further 4 hours to accomplish the carboxyl-protecting reaction. The reaction solution was then concentrated by evaporation under reduced pressure, washed with 200 ml of a mixture of petroleum ether/ethyl ether (1:1) and evaporated to dryness to give 7.6 g of 7β-[5D-5-(trichloroethoxycarbonylamino)-5-(diphenylmethyloxycarbonyl)-valerylamido]-7α-methoxy-3-[(1-methyl-1H-tetrazole-5-yl)thiomethyl]-3-cephem-4-carboxylic acid diphenylmethyl ester.

This product showed Rf value=0.47 when developed in a thin layer chromatography on silica gel using a solvent of benzene/acetone (1:1).

(iii) 3 g of the product prepared in the above procedure (ii) was dissolved in 70 ml of dichloromethane, to which were then added 6 g of "Molecular Sieves" 4A and 2.4 g of bromoacetyl bromide. The mixture was agitated at 40° C. for 10 hours, followed by further addition of 6 g of "Molecular Sieves" 4A and agitation at 40° C. for further 10 hours.

The resulting reaction mixture was cooled and filtered to remove insoluble matters. The filtrate was concentrated by evaporation under reduced pressure, washed with hexane and further concentrated to dryness. The residue was taken up in 20 ml of ethyl acetate and the solution was admixed with 20 ml of 90% aqueous acetic acid and 2 g of zinc dust. The admixture was allowed to stand at 0°~5° C. for 5 hours for the purpose of removing the trichloroethoxycarbonyl group from the terminal amino group. Thereafter, the reaction solution was filtered to remove the insoluble matters and ethyl acetate was added to the filtrate to a total volume of 150 ml. The solution was washed with 5% aqueous sodium bicarbonate and then aqueous saturated sodium chloride, dried over anhydrous sodium sulfate and evaporated to dryness to leave 1.95 g of a crude product. The crude product was purified by column chromatography on Sephadex LH-20 (a gel-filtration agent, a product of Pharmacia Chemical Co., Sweden) developed with a mixture of ethyl acetate/methanol (50:1) as the developing solvent to afford 1.1 g of 7β-bromoacetamide-7α-methoxy-3-[(1-methyl-1H-tetrazole-5-yl)thiomethyl]-3-cephem-4-carboxylic acid diphenylmethyl ester.

This product showed Rf value=0.5 when developed in a thin layer chromatography on silica gel using a solvent of toluene/ethyl acetate (5:4).

(iv) Alternatively to the above procedure (iii), 1.5 g of the product obtained in the aforesaid procedure (ii) was dissolved in 30 ml of dichloromethane, to which was then added 2 ml of N,N-bis(trimethylsilyl)-trifluoroacetamide (as the silylating agent). The mixture was agitated at 40° C. for 2 hours, followed by addition of 1.2 g of bromoacetyl bromide and continued agitation of the mixture for further 48 hours.

After the completion of the reaction, the reaction solution was evaporated under reduced pressure, then washed with hexane and concentrated to dryness. The residue was taken up in 7 ml of ethyl acetate and the solution was admixed with 7 ml of 90% aqueous acetic acid and 2.5 g of zinc dust. The admixture was allowed to stand at ambient temperature for 4 hours to effect the N-deprotecting reaction at the terminal amino group.

The reaction solution was filtered and washed with ethyl acetate. 100 ml of the filtrate was washed with 5% aqueous sodium bicarbonate and water, dried over anhydrous sodium sulfate and concentrated to dryness to give 0.98 g of a crude product.

The crude product was purified by column chromatography on Sephadex LH-20 using a developing solvent of ethyl acetate/methanol (50:1) to yield 450 mg of 7β-bromoacetamide-7α-methoxy-3-[(1-methyl-1H-tetrazole-5-yl)thiomethyl]-3-cephem-4-carboxylic acid diphenylmethyl ester.

(v) 1.2 g of the product prepared in the above procedure (iii) or (iv) was dissolved in 10 ml of anisole and to the solution was added 12.5 ml of trifluoroacetic acid under ice-cooling and stirring. After the reaction of removing the carboxyl-protecting diphenylmethyl group was effected for 30 minutes, the reaction solution was evaporated under reduced pressure without heating. The residue was taken up in 100 ml of ethyl acetate and the solution was extracted with 150 ml of 10% aqueous dipotassium phosphate.

The extract was washed with ethyl acetate and admixed with 100 ml of ethyl acetate, followed by addition of 5 N hydrochloric acid under agitation and cooling. The resultant aqueous layer was adjusted to pH 2.0 by addition of 5 N-HCl before separation of the ethyl acetate layer and then extracted with further ethyl acetate. the combined organic layer was washed with aqueous saturated sodium chloride, dried over anhydrous magnesium sulfate and concentrated to dryness to give 560 mg of 7β-bromoacetamide-7α-methoxy-3-[(1-methyl-1H-tetrazole-5-yl) thiomethyl]-3-cephem-4-carboxylic acid.

This product indicated Rf value=0.68 when developed in a T.L.C. on silica gel using a mixed solvent of n-butanol/acetic acid/water (2:1:1).

(vi) 480 mg of the product obtained in the above procedure (v) was suspended in 10 ml of water, to which was added aqueous saturated sodium bicarbonate to adjust the suspension to pH 7.0, thereby forming a solution. 210 mg of D-cysteine hydrochloride was added to the solution and the mixture was allowed to stand at ambient temperature for one hour with maintenance at pH 7.0~7.5 by occasional addition of aqueous NaHCO₃. Thereafter, the reaction mixture containing 7β-[(2D-2-amino-2-carboxy)ethylthioacetamido]-7α-methoxy-3-[(1-methyl-1H-tetrazole-5-yl)thiomethyl]-3-cephem-4-carboxylic acid produced was adjusted to pH 6.0 by addition of 5 N—HCl and passed through a column of Diaion HP-20 (100 ml) to adsorb the desired product on the resin. The resin was then eluted with water and the eluate fractions containing the desired product were concentrated and freeze-dried to yield 260 mg of sodium 7β-[(2D-2-amino-2-carboxy)ethylthioacetamido]-7α-methoxy-3-[(1-methyl-1H-tetrazole-5-yl)thiomethyl]-3-cephem-4-carboxylate.

The final product indicated Rf value=0.41 when developed in thin layer chromatography on silica gel using a mixed solvent of n-butanol/acetic acid/water (2:1:1 by volume).

What we claim is:

1. A process for the production of 7β-[(2D-2-amino-2-carboxy)ethylthioacetamido]-7α-methoxy-3-[(1-methyl-1H-tetrazole-5-yl)thiomethyl]-3-cephem-4-carboxylic acid which comprises the consecutive steps of:

(a) reacting cephamycin A and/or cephamycin B with 5-mercapto-1-methyl-1H-tetrazole to produce the compound of the formula (I)

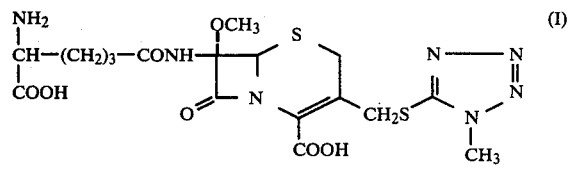

(b) reacting the compound (I) with an acylating agent for introduction of an amino-protecting group to produce a compound of the formula (II)

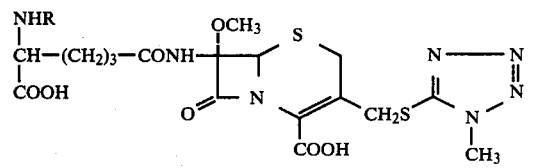

wherein R represents the amino-protecting group of acyl type, (c) reacting the compound (II) with a reagent for introduction of a carboxyl-protecting group to block the two carboxyl groups of the compound (II) and produce the compound of the formula (II′)

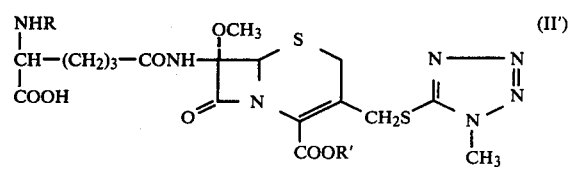

wherein R′ represents the carboxyl-protecting group, (d) reacting the compound (II′) with a halogenoacetyl halide of the formula

XCH₂COX′ wherein X and X′, which may be the same or different, each represents a halogen, particularly chlorine or bromine, in the presence of a molecular sieves material or in the presence of a silylating agent to produce a compound of the formula

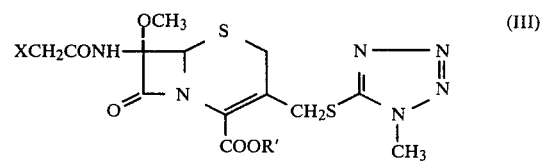

wherein X is as defined above and R′ represents the carboxylprotecting group as above, (e) removing the carboxyl-protecting group (R′) from the compound (III) in a known manner to produce the compound of the formula (III′)

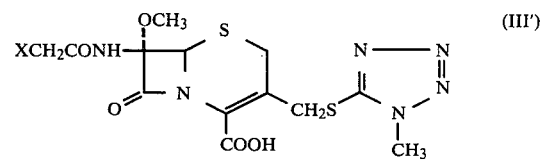

wherein X is as defined above, and (f) reacting the compound (III′) with D-cysteine to produce the desired product.

2. A process as claimed in claim 1 which further include the step of reacting the desired product of the process of claim 1 with a pharmaceutically acceptable cation to produce the corresponding pharmaceutically acceptable salt.

3. A process as claimed in claim 1 in which the step (a) is carried out by reacting 5-mercapto-1-methyl-1H-tetrazole with cephamycin A and/or cephamycin B which are or is present still in the filtrate of the culture broth of *Streptomyces viridochromogenes* SF-1584 (FERM-P No. 2284) or in a concentrated solution of said filtrate.

4. A process as claimed in claim 1 in which the step (a) is carried out at a temperature of 15°~60° C. under neutral or acidic conditions in an aqueous solution containing cephamycin A and/or cephamycin B.

5. A process as claimed in claim 1 in which the acylating agent for introduction of the amino-protecting group employed in the step (b) is trichloroethoxycarbonyl chloride.

6. A process as claimed in claim 1 in which the reagent for introduction of the carboxyl-protecting group employed in the step (c) is an esterification agent selected from diphenyldiazomethane, isobutene, trichloroethyl chloride, methoxyethoxymethyl chloride or a p-nitrobenzyl bromide.

7. A process as claimed in claim 1 in which the step (d) for reaction of the halogenoacetyl halide with the compound (II′) is carried out in an aprotic organic solvent at a temperature of 15°~60° C. in the presence of a synthetic zeolite as the molecular sieves material or in the presence of a silylating agent which is selected from N-(trimethylsilyl)acetamide, N,N-bis(trimethylsilyl- )acetamide and N,N-bis(trimethylsilyl)trifluoroacetamide.

8. A process as claimed in claim 1 in which the step (e) for removal of the carboxyl-protecting group is carried out in a known manner by alcoholysis, by hydrolysis or by catalytic hydrogenolysis according to the nature of the carboxyl-protecting group to be removed.

9. A process as claimed in claim 1 in which the step (f) for reaction of D-cysteine with the compound (III′) is carried out at a temperature of 0° to 30° C. in water or in an aqueous, inert organic solvent under neutral conditions.

* * * * *